(12) United States Patent
Christiansen (10) Patent No.: US 7,160,712 B2
(45) Date of Patent: Jan. 9, 2007

(54) ODOR CONTROL

(75) Inventor: John A. Christiansen, The Woodlands, TX (US)

(73) Assignee: Novozymes A/S (DK)

( * ) Notice: Subject to any disclaimer, the term of this patent is extended or adjusted under 35 U.S.C. 154(b) by 227 days.

(21) Appl. No.: 10/230,792

(22) Filed: Aug. 29, 2002

(65) Prior Publication Data

US 2004/0180424 A1 Sep. 16, 2004

Related U.S. Application Data

(63) Continuation of application No. 09/400,229, filed on Sep. 21, 1999, now abandoned.

(51) Int. Cl.
*C02F 3/34* (2006.01)
(52) U.S. Cl. ............. 435/262; 435/266; 210/606; 210/610; 210/611; 210/916
(58) Field of Classification Search ........... 210/603, 210/611, 614, 916
See application file for complete search history.

(56) References Cited

U.S. PATENT DOCUMENTS 6,221,652 B1 * 4/2001 Janssen et al. ............. 435/266

6,410,305 B1 * 6/2002 Miller et al. ............. 435/268

OTHER PUBLICATIONS

Jordan S.L., et al. "Autotrophic growth on carbon disulfide is a property of novel strains of *Paracoccus denitrificans*", Archives of Microbiology, (Sep. 1997) vol. 168, No. 3, pp. 225-236.*

* cited by examiner

*Primary Examiner*—David Redding
(74) *Attorney, Agent, or Firm*—Roy, Kiesel, Keegan & DeNicola (57) ABSTRACT

Disclosed herein is a method for treating odors in wastewater treatment bodies. The pH of the body is preferably established above about 6 and most preferably above about 7, usually by adding a base to the body. The oxidation reduction potential of the body is established at about −300 mV or higher and more preferably about −200 mV or higher, usually by adding an oxidizing agent such as oxygen or nitrates. After these conditions are established, sulfur oxidizing bacteria are added to the body. These preferably include *Paracoccus denitrificans* (formerly called *Thiosphaera pantotropha*) ATTC number 35,512. The sulfur oxidizing bacterial population should be established at levels of at least about $1\times10^4$ cfu/mL and more preferably at levels of $1\times10^5$ to $1\times10^6$ cfu/mL or higher. The increased ORP and pH levels make sulfate reduction thermodynamically unfavorable. Additionally, the presence of an alternative electron acceptor such as oxygen or nitrate allows the sulfur oxidizing bacteria to oxidize organic acids.

17 Claims, 7 Drawing Sheets

☐ = Low ORP "Hot Spot"

ODOR CONTROL

HISTORY OF THE APPLICATION

This is a continuation of U.S. application Ser. No. 09/400,229, filed Sep. 21, 1999, which is hereby incorporated by reference in its entirety, now abandoned.

BACKGROUND OF THE INVENTION

1. Field of the Invention

The invention relates to wastewater treatment in general and to methods of controlling odors during treatment in particular.

2. Prior Art

Objectionable odors are caused by a variety of substances typically present in wastewater. These include sulfur and several sulfur containing compounds including hydro sulfuric acid, sulfuric acid, mercaptans (R—SH) including especially methyl and dimethyl mercaptans, and dimethyl disulfide (DMDS); numerous organic acids including propionic acid, acetic acid, butyric acid, isovaleric acid; ammonia; urea; and various terpenes including carene, pinene, limonene. These substances most frequently lead to noticeable odors under anaerobic conditions.

There are several approaches to odor problems known in the art. One solution is to add masking agents and perfumes to the wastewater. Obviously, such measures do not solve the problem, but only cover it up. Another solution is to add aerating equipment. These measures are frequently successful, but they can be very expensive, both from the standpoint of capital spent on the equipment itself and in terms of increased operating expense.

Chemical oxidizers, such as ozone; chlorine dioxide; and hydrogen, calcium, or magnesium peroxide, may be added to wastewater to alleviate anaerobic conditions. Although these methods can be effective, they are usually very expensive. This expense pressures managers of wastewater facilities to minimize the amount of oxidizers added to the system. The need to economize can be detrimental if it leads to underdosing. Underdosing can cause incomplete or partial oxidation, which can create worse odor problems than those the oxidants were introduced to cure. When chlorine dioxide is added to organic acids, incomplete oxidation can cause the formation of chloroacetic acid, which has a foul odor noticeable at very low concentrations.

Another method is to add neutralizing amines, which form stable salts with sulfide compounds. These may be effective against sulfide compounds, but do not treat other sources of odors such as organic acids. Additionally, amines suffer the same disadvantage as all chemical treatments. The chemicals are consumed in the reaction with the sulfur compounds in the wastewater, requiring new chemicals to be added if more sulfur compounds enter the wastewater treatment facility.

It is also known to add bacteria and enzymes to the wastewater to combat the odor causing substances. Again, these methods are frequently effective, but their results are often short lived. Typically, the evolution of odors from wastewater treatment lagoons will be due at least in part to the presence of undesirable bacteria in the lagoon. Unless the conditions that gave rise to the undesirable bacteria are rectified, the newly added bacteria will usually not be able to predominate, and the bacterial population will eventually return to its pre-treatment composition. As that occurs, the odors associated with the original population will return as well. Accordingly, an odor control method meeting the following objectives is desired.

OBJECTS OF THE INVENTION

It is an object of the invention to reduce or eliminate odors in wastewater treatment plants.

It is another object of the invention to correct the conditions that lead to odor formation in wastewater treatment plants.

It is another object of the invention to prevent the reduction of $SO_4^{2-}$.

It is still another object of the invention to change the microbial population of the wastewater treatment from sulfur reducing bacteria to sulfur oxidizing bacteria.

It is still another object of the invention to biologically oxidize organic acids present in the wastewater.

It is still another object of the invention to provide an odor treatment method that is capable of simultaneously treating $BOD_5$.

It is yet another object of the invention to minimize the expense associated with odor treatment in wastewater treatment plants.

SUMMARY OF THE INVENTION

When odor problems arise, the bacterial population frequently contains high concentrations of sulfide reducers, bacteria able to use $SO_4^{2-}$ or other sulfur containing compounds as terminal electron acceptor when there is insufficient oxygen present in the water. These bacteria reduce the sulfur in $SO_4^{2-}$ ($S^{6+}$) to ($S^{2-}$) which exists as $H_2S$, bisulfide, ($HS^-$) and mercaptans, in wastewater. These are the sources of some of the worst odors associated with industrial waste treatment. To treat this condition, the inventor alters the water chemistry in order to make the reduction of sulfur chemical species thermodynamically unfavorable, and he adds bacteria, preferably *Paracoccus pantotrophus* (formerly called *Thiosphaera pantotropha*), capable of oxidizing sulfide, ($S^{2-}$) to elemental sulfur ($S^0$), ($S^{4+}$) which exists as sulfite ($SO_3^{2-}$), or ($S^{6+}$) which exists as sulfate $SO_4^{2-}$.

Both the sulfur oxidizing and reducing bacteria use soluble organic matter—measured in terms of five day biochemical oxygen demand or $BOD_5$—as an energy source. Some bacteria, such as *Paracoccus pantotrophus* can use reduced sulfur compounds (i.e., $H_2S$, bisulfide and mercaptans) as their energy source. Such bacteria also need an electron acceptor to metabolize the energy sources. The nature of the electron acceptor present in the wastewater often "selects" the microbial culture that thrives in the environment. The most energetically favorable reaction in waste water is usually the reduction of oxygen ($O_2$) to water ($H_2O$). The presence of dissolved oxygen in the wastewater will often allow bacteria that are not capable of using sulfur compounds as a terminal electron acceptor to metabolize the organic matter in the wastewater. Additionally, most sulfur reducing bacteria are capable of using oxygen rather than sulfur as the terminal electron acceptor, and will use oxygen when sufficient amounts are available in the wastewater.

When there is insufficient oxygen present, sulfur reducing bacteria use the sulfur in sulfate ($SO_4^{2-}$) containing compounds as the terminal electron acceptor and produce hydrogen sulfide ($H_2S$) in the process. In order to prevent this from happening, the inventor alters the water chemistry to make conditions unfavorable for sulfate reduction.

The inventor provides another chemical that is capable of serving as the terminal electron acceptor and whose reduction is more energetically favorable than the reduction of sulfate. Preferably, these are chemicals which most sulfur reducing bacteria cannot use as an electron acceptor. Examples include nitrate $NO_3^-$ which can be biologically reduced to nitrogen gas $N_2$ and hydrogen peroxide $H_2O_2$ which can then be biologically reduced to water. The addition of these chemicals to the wastewater, in combination with bacteria present or added, will change the oxidation reduction potential (ORP) of the wastewater. The target ORP range is about −330 mV to +100 mV. In addition to changing ORP, the inventor will usually alter the pH. The target pH range is about 6.0 to about 8.2. The target ORP and the target pH values are inversely related; the lower the pH, the higher the desired ORP levels and vice versa.

Under these modified chemical conditions, the evolution of hydrogen sulfide gas is inhibited, the reduction of sulfur is made more difficult, and the ability of sulfur reducing bacteria to metabolize $BOD_5$ sources is inhibited. However, conditions are also made favorable for sulfur oxidizing bacteria capable of using the nitrates or peroxides as a terminal electron source, such as *Paracoccus pantotrophus*. If provided in high concentrations, the sulfur oxidizing bacteria should be able to take over the ecological niche of the sulfur reducers.

Like sulfur compounds, organic acids also create odor problems in wastewater. Under anaerobic conditions, the bacterial population can form butyric, isovaleric, and propionic acids from more complex organic acids. In turn, these acids can be converted into acetic acid. If conditions remain anaerobic, methanogenic bacteria will convert the acetic acids into methane. However, oxygen is toxic to methanogens, even at very low concentrations, (~0.2 mg/L and higher). Thus, an increase in the oxygen concentration in the wastewater can stop the conversion of acetic acid to methane.

Many industrial waste treatment facilities are large lagoons. Although these lagoons may have dissolved oxygen levels that are, on average, extremely low, they are almost invariably open to the atmosphere. Thus, there is no barrier to the diffusion of oxygen through the lagoon surface. This can lead to oxygen concentrations sufficient to prevent the conversion of acetic acid to methane, either across the entire lagoon, or at different locations throughout the lagoon. As the oxygen levels increase, perhaps in only a few isolated portions of the lagoon, the acetic acid concentrations will increase. The acetic acid build up will effect the equilibrium of the conversion of butyric, isovaleric, and propionic acid to acetic acid, leading to an increase in the concentrations of these acids as well.

Acetic acid, butyric acid, isovaleric acid, and propionic acid all have a rancid smell. As their concentrations rise, their respective gases will begin to evaporate from the lagoon, creating objectionable odors for those that live and work nearby. To counter this problem, the inventor adds a bacteria capable of oxidizing the acids, such as *Paracoccus pantotrophus*. As with odors caused by sulfur compounds, the ORP usually must be raised to allow the *P. pantotrophus* to oxidize the organic acids. This is done by adding a terminal electron acceptor such as nitrate or hydrogen peroxide to raise the ORP levels to between about −330 mV and about +100 mV, depending upon pH. The preferred ORP level will vary depending upon the pH of the system.

It should be understood that although the inventor describes the increase in ORP in terms of the chemicals added, this is largely a biochemical process. The addition of alternative electron acceptors allows bacteria to change the ORP of the wastewater. Where the bacteria present in the system are incapable of reducing nitrate (or other alternate electron acceptors) or of oxidizing sulfur, the inventor adds them in order to facilitate reduction of the electron acceptors and thereby allow ORP to be increased. At the increased ORP's, the reduction of sulfur is no longer as thermodynamically advantageous for bacteria, and bacteria more efficient at using other electron acceptors will predominate over bacteria particularly suited to using sulfur.

DETAILED DESCRIPTION OF THE PREFERRED EMBODIMENTS

In the preferred embodiment of the invention, the wastewater is tested as an initial matter. The water should be analyzed to determine pH; temperature; ORP; total sulfur content and speciation—the identification of relative quantities of sulfide ($S^{2-}$) vs. sulfate ($SO_4^{2-}$); nitrogen content and speciation—the identification of relative quantities of nitrate ($NO_3^-$), nitrogen ($N_2$), and ammonia ($NH_3$); and organic concentration. For lagoons and other large treatment bodies, samples should be taken at several different locations in order to obtain an accurate picture of conditions across the entire body.

Systems with a noticeable rancid odor, pH levels below about 7, ORP levels below about −250 mV, and a sulfide content above about 3.0 mg/L ($S^{2-}$) are the principal candidates for the treatment described herein. If sulfide levels are below about 3.0 mg/L, but total sulfur content is about 1000 mg/L or higher, treatment may be appropriate because of the potential for the formation of sulfides and the associated odors. Systems with nitrate concentrations above about 2.0 mg/L may also be appropriate candidates if the bacterial population is incapable of reducing the nitrate. In all cases $BOD_5$ should be about 50 mg/L or higher in order to provide an adequate energy source for the bacteria.

Figure 1:
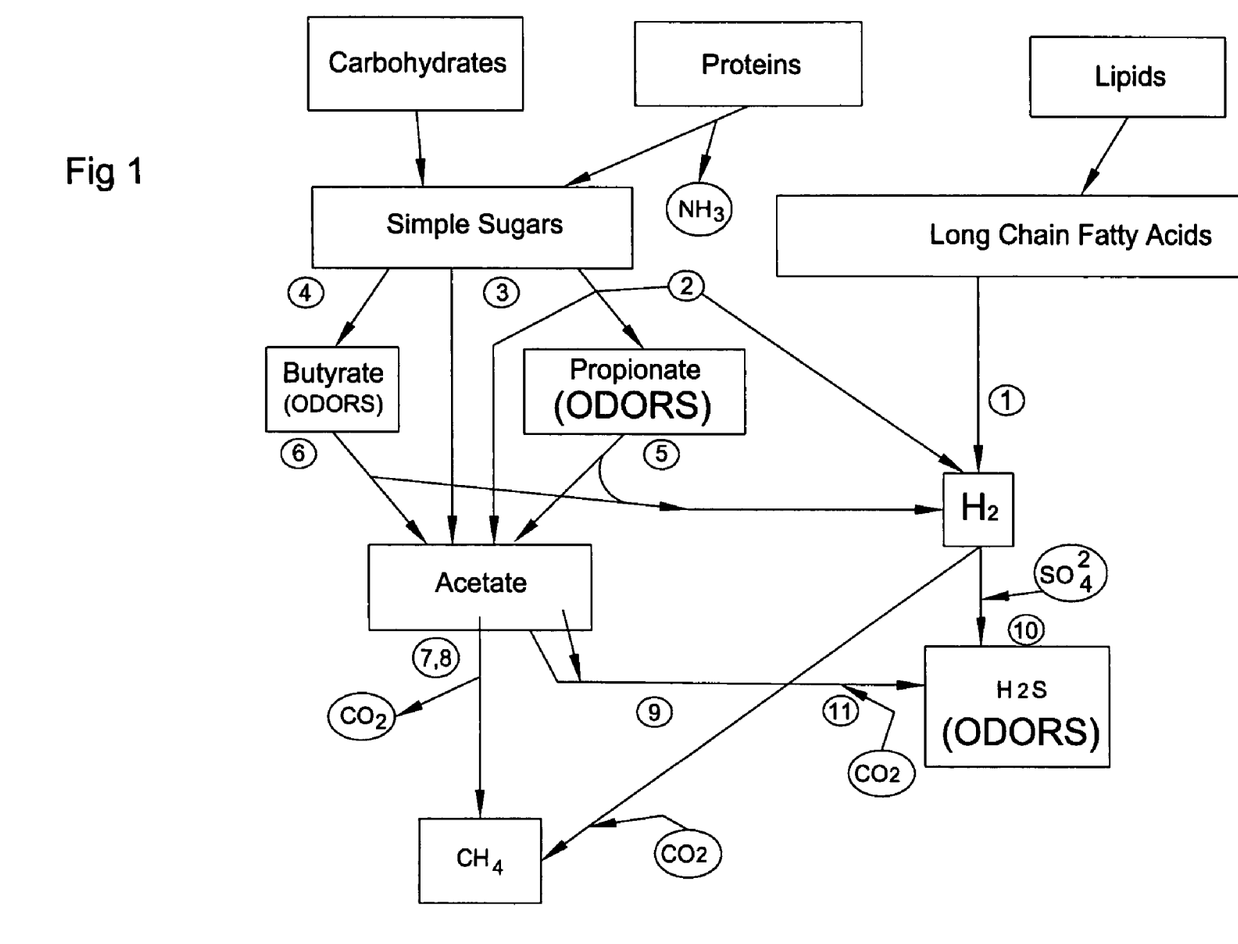
FIG. 1 is a graphical representation of the biochemical pathway by which numerous wastewater components are broken down during anaerobic biological treatment.
Figure 2:
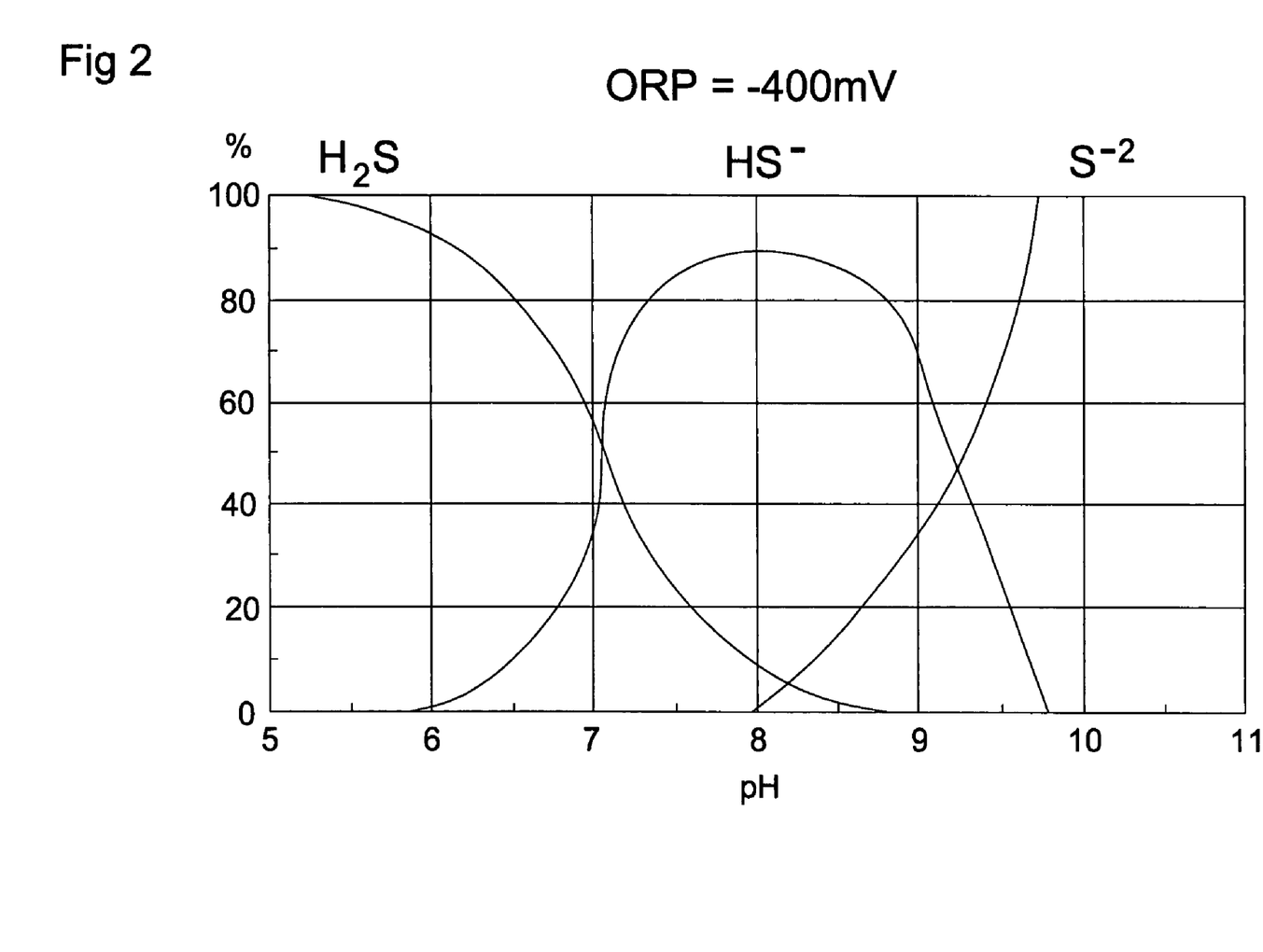
FIG. 2 is a graphical representation of how equilibrium between the various forms of sulfide changes as pH is changed if ORP is held constant at −400 mV.
Figure 3:
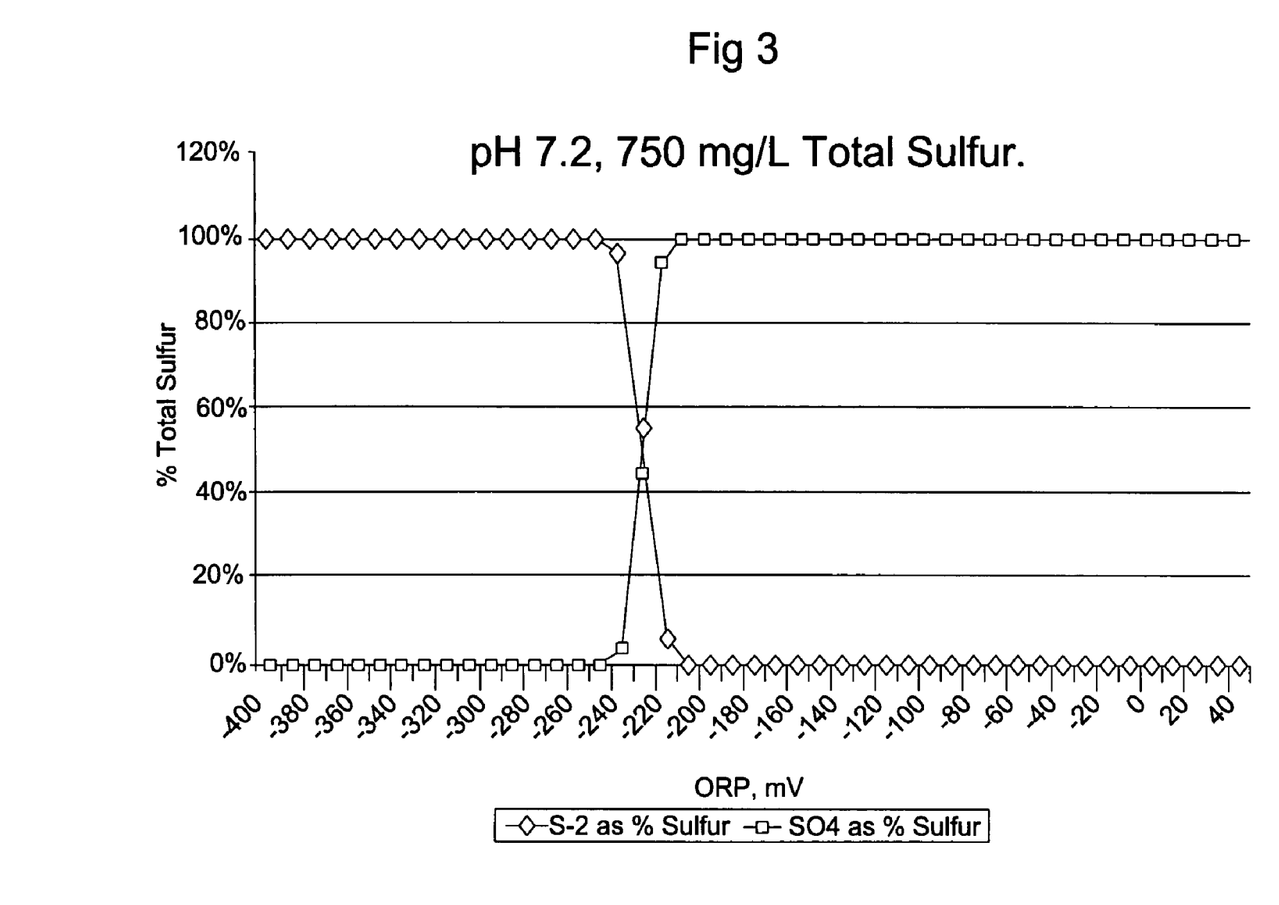
FIG. 3 is a graphical representation of how the equilibrium between the sulfide and sulfate forms of sulfur varies with ORP if pH is held constant at 7.2 and total sulfur is held constant at 750 mg/L.

The overriding goals are the prevention of odors by creating an environment thermodynamically favorable to the growth of sulfur oxidizing bacteria and thermodynamically unfavorable to the growth of sulfur reducing bacteria. The first step is to establish pH levels that will inhibit the volatilization of sulfides ($S^{2-}$). As illustrated in FIG. 2, equilibrium between $H_2S$ and $HS^-$ strongly favors $HS^-$ at pH values above about 7.2. As ORP increases, this equilibrium point shifts toward a lower pH value. Thus, by increasing the pH (or increasing the ORP) the predominant form of sulfide ($S^{2-}$) can be changed from $H_2S$ to $HS^-$ or to $S^{2-}$. Both of these latter forms of sulfide ($S^{2-}$) are much less volatile than the hydrogen sulfide molecule, and thus less likely to be evolved from the wastewater treatment facility as a gas.

In the situation where sulfur odors are a problem, the wastewater will typically be somewhat acidic. Thus, bases will usually required, although acids may be added if the pH is too high. Suitable bases include carbonates ($NaHCO_3$, $K_2CO_3$, or $Na_2CO_3$), caustics (NaOH or KOH), and solid hydroxides ($Ca(OH)_2*xH_2O$) such as lime, hydrated lime, quick lime, and slaked lime. Sufficient quantities should be added to increase the pH of the wastewater to levels of between about 6 and about 8.2, and preferably to between about 7 and about 7.5, and most preferably to a pH of about 7.2. The specific quantities needed must be determined on a case-by-case basis and will depend on the volume of the body being treated, its pH, and the concentration of the additive.

After pH is fixed, the ORP levels should be increased to a suitable level, although it should be noted that these two steps may be reversed. ORP controls the valence levels of the sulfur molecule which can vary from 2− to 6+. This in turn controls the sulfur speciation in the wastewater. For example, $H_2S$, which is odor causing, requires sulfur with a valence level of 2− ($S^{2-}$). On the other hand, $SO_4^{2-}$, which is not odor causing, requires sulfur with a valence level of 6+ ($S^{6+}$). By changing the ORP in the wastewater, the inventor can alter the species of sulfur present, and thus prevent the formation of odor causing sulfur species.

Figure 10:
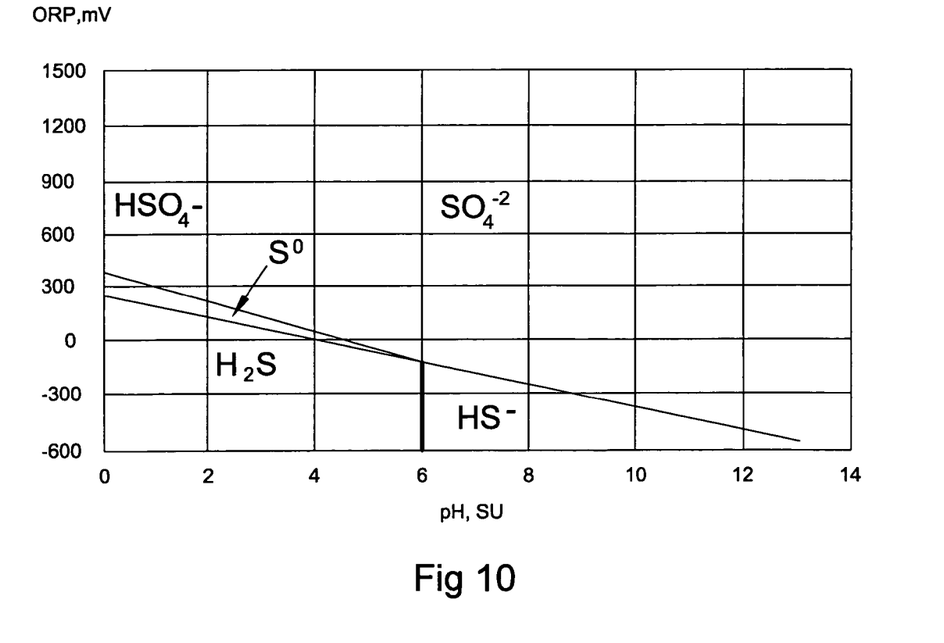
FIG. 10 is a graphical illustration of how the dominant form of sulfur in 0.02M sulfur solutions changes with ORP and pH.

As illustrated in FIG. 10, at pH levels above about 7 and ORP's in the −300 to −200 mV range or higher, the predominant form of sulfur is sulfate ($SO_4^{2-}$) or bisulfide ($HS^-$). At these ORP and pH levels, sulfate is not easily reduced to sulfide, which keeps the bisulfide concentration low. With low bisulfide concentrations and pH levels above 7.0, hydrogen sulfide will not readily form and hydrogen sulfide gas will not readily evolve from the wastewater. Therefore, sufficient quantities of oxidizing agent should be added to the wastewater to raise the ORP to at least about −200 mV and preferably to about −150 mV or higher, although preferably not beyond about +100 mV where nitrate is used. Above that level, the reduction of nitrate becomes impaired. Some suitable oxidizing agents include oxygen $O_2$; ozone $O_3$; peroxides including hydrogen peroxide $H_2O_2$, calcium peroxide $CaO_2*xH_2O$, and magnesium peroxide $MgO_2*xH_2O$; nitrates $R(NO_3)_x$; nitrites $RNO_2$, permanganate $KMnO_4$, potassium dichromate $K_2Cr_2O_7$, potassium chlorate $KClO_3$, and chlorine dioxide $ClO_2$. The inventor's preferred oxidizing agents are nitrate salts, such as calcium nitrate $Ca(NO_3)_2*4H_2O$ or sodium nitrate $NaNO_3$.

It will usually be desirable to increase ORP rapidly in order to eliminate odors as quickly as possible. To this end, it will usually be preferable to add large doses of oxidizing agent initially. The specific amount needed must be calculated for each wastewater facility. The necessary quantity will depend upon the volume of the body being treated; its current ORP; the target ORP; the concentration of the additive; temperature (which affects the equilibrium point of chemical species as well as the rate at which biological processes occur); the concentration of total organic acids, particularly acetic, butyric, isovaleric, and proprionic acids; the total sulfur concentration; and the total concentration of odor causing sulfur species such as sulfides and mercaptans—note that the total sulfur concentration will necessarily effect the total concentration of odor causing sulfur species. In the inventor's experience, total sulfur will vary from about 200 to about 1100 mg of total sulfur per liter of wastewater, although higher concentrations may be encountered. The inventor expects concentrations of about 20 to about 30 mg/L $NO_3^-$ [160 to 240 lbs. $NO_3^-$ per gallon of basin volume—or per million gallon per day (mgd)—flow rate] to be sufficient as an initial treatment dosage where pH is about 7 and ORP is between about −100 mV and −300 mV. The inventor usually applies the initial oxidizing agent as a dry solid comprising either 72% by weight sodium nitrate granules or 50% by weight calcium nitrate granules.

The oxidizing agent may be added to the influent of a lagoon, clarifier, wet well (the sump area where pumps apply suction in a lift station), or other wastewater treatment facility. In large lagoons, it may be desirable to broadcast the oxidizing agent over the lagoon in order to avoid waiting for the agent to disperse throughout the lagoon. Aircraft, watercraft, shore based spraying units, and other conventional means of broadcasting may be used to apply the oxidizing agent to the lagoon. Rather than adding the agent to the entire lagoon, it may be desirable to add it to areas in the lagoon where the ORP is the most depressed. Although this should be determined through actual measurements, the inventor has discovered that this point will frequently be removed from the influent point of the lagoon by about one third the length of the lagoon.

After the initial ORP treatment, additional oxidizing agent will usually need to be added to the system on a maintenance basis. The inventor typically uses a liquid sodium nitrate or calcium nitrate solution for maintenance doses. As with the initial treatment, the maintenance doses may be added with the influent, broadcast over the facility, or added to the point where ORP is most depressed. It will generally not be necessary to broadcast maintenance doses, as ORP should already be elevated by the time maintenance doses are added; however, if a rapid increase in ORP is needed, broadcasting maintenance doses may be desirable. Adding oxidizing agents at the lowest ORP point may minimize the amount of agent needed for maintenance, although this must be determined for each facility.

As with the initial treatment, the size of the doses needed for maintenance purposes will vary from lagoon to lagoon, and must be individually calculated. However, the inventor expects that about 1.2 mg $NO_3^-$ per liter of lagoon volume, preferably provided from a liquid nitrate solution, to be suitable to maintain the desired ORP level. The nitrate may be provided from several sources. The preferred liquid sources are a sodium nitrate solution containing about 6 lbs. of $NO_3^-$ per gallon of solution or a calcium nitrate solution with about 3.9 lbs of $NO_{3_-}$ per gallon or about 70% $Ca(NO_3)_2.4H_2O$, by weight, per gallon of solution. Expressed in terms of flow rate, the inventor expects 8 to 30 gallons of the above listed sodium nitrate solution per mgd or 10 to 50 gallons of the above listed calcium nitrate solution per mgd to be sufficient for maintenance.

After the chemicals for modifying pH and ORP have been added, sulfur oxidizing bacteria are added to the wastewater. It is usually preferable to introduce the sulfur oxidizing bacteria immediately after the ORP chemicals have been added to the wastewater. Where pH and ORP altering chemicals are added in large initial treatments over the course of several days, it is usually preferable to add the sulfur oxidizing bacteria after each pH and ORP treatment.

The principle sulfur oxidizing bacteria contemplated for use by the inventor is *Paracoccus pantotrophus* (formerly *Thiosphaera pantotrophia*) ATCC # 35512. *P. pantotrophus* is preferably introduced in a culture containing several other nutrients. Depending upon the characteristics of the wastewater, it may be desirable to add some nutrients or other additives to the wastewater in order to foster growth of the bacteria.

Some additives that may be introduced either with the bacterial culture or independently to the wastewater include coral sand, available from Worldwide Imports, 5315 Northwest 10 Terrace, Ft. Lauderdale, Fla. 33309; Triton X-100 (TX-100), available from Van, Waters & Rogers, 777 Brisbane, Houston, Tex. 77061; diatomaceous earth (Diafil 110), available from D&F Distribution, 10201 Northwest Freeway, Suite 212, Houston Tex. 77092; and Plurafac A38 (CAS 69227-21-0), available from Van, Waters & Rogers, 777 Brisbane, Houston, Tex. 77061. Coral sand provides a high surface area for initial colony formation. About 0.10 to 0.30 pounds of coral sand per pound of bacteria culture is generally sufficient. The diatomaceous earth is a preservative used to prevent insect contamination of the bran during storage. The TX-100 is a wetting agent used to promote thorough mixing of the bacteria during culture preparation. Both the diatomaceous earth and the TX-100 should preferably be provided in ratios of about 0.015 to 0.035 pounds per pound of bacteria culture. Plurafac is a surfactant which acts as a dust control agent. About 0.0013 to about 0.013 pounds of Plurafac per pound of bacteria culture is generally sufficient. When cultures exceed the desired concentration, they can be reduced by the addition of wheat shorts. The specification for the inventor's preferred culture is provided below.

TABLE A

| | Quantity |
|---|---|
| Bacteria | |
| *Paracoccus pantotrophus* minimum (formerly *Thiosphaera pantotrophia*) (ATCC 35512) | $2.80 \times 10^8$ cfu/gm ($1.27 \times 10^{11}$ cfu/lb) after at least 24 hrs. incubation at 35° C. |
| Other Materials | |
| Coral Sand | 0.20 lb/lb (20% by weight of culture) |
| TX-100 | 0.025 lb/lb (2.5% by weight of culture) |
| Diatomaceous Earth (Diafil 110) | 0.005 lb/lb (0.5% by weight of culture) |
| Plurafac A38 (CAS 69227-21-0) | 0.0013 lb/lb (0.13% by weight of culture) |
| Wheat Shorts | 0.77 lb/lb - approx. - add to 100% |

*Paracoccus pantotrophus* is capable of aerobic or facultative anaerobic respiration, meaning that it can use $O_2$ or $NO_3^-$ as an electron acceptor. This provides *Paracoccus pantotrophus* with an advantage over most other sulfur oxidizing bacteria, as well as most sulfur reducing bacteria, because few of either class of bacteria share this trait. When nitrate is added to the system, the *Paracoccus pantotrophus* will use the $NO_3^-$ as an electron acceptor and will use sulfide ions as an electron donor. It will oxidize sulfide, in progressive order, to elemental sulfur $S^0$, thiosulfate $S_2O_3^{2-}$, tetrathionate $S_4O_6^{2-}$, sulfite $SO_3^{2-}$ and sulfate $SO_4^{2-}$ as increasing moles of oxygen are available. None of these oxidized sulfur forms are odor causing. If sufficient electron acceptors are maintained in the wastewater, the *Paracoccus pantotrophus* will become established in the system and predominate over the sulfur reducing bacteria, preventing future odor problems.

Like the oxidizing agents discussed above, it will typically be desirable to provide a large initial dose of the sulfur oxidizing bacteria to the treatment facility. This may be added to the influent stream or broadcast over the entire treatment body. For bodies such as large lagoons, broadcasting will generally be preferable.

The amount of sulfur oxidizing bacteria required will vary with the amount of BOD in the water, the temperature of the wastewater, the ORP of the wastewater, the volume of the treatment body, and the flow rate through the body. This amount will have to be determined on a case-by-case basis; however, for lagoons the inventor expects that initial treatment doses of between about 10 to about 25 lbs of the preferred culture per acre per day (about $1.27 \times 10^{12}$ to about $3.178 \times 10^{12}$ cfu/acre/day—note that all units given in terms of acreage assume a lagoon depth of about ten feet) for the first three to four days should be sufficient. The inventor expects clarifiers and wet wells to generally require lower initial doses: between about 5 to about 15 lbs of the preferred culture per mgd (about $6.36 \times 10^{11}$ to about $1.91 \times 10^{12}$ cfu/mgd) and most preferably about 10 lbs per mgd (about $1.27 \times 10^{12}$ cfu/mgd).

Initial doses of the sulfur oxidizing bacteria should preferably be provided immediately after each initial dose of oxidizing agents and pH additives. The inventor expects one to three or four days worth of initial doses to be sufficient, because the bacteria will reproduce at an exponential rate. For example, an initial dose of $1.0 \times 10^{11}$ cfu per million gallons of lagoon volume would grow to $3.8 \times 10^{15}$ to $3.8 \times 10^{17}$ cfu per million gallons of lagoon volume in about 72 hours. However, the rate of reproduction is affected by numerous different factors, including temperature, $BOD_5$, oxygen concentration, nutrients, pH, etc. Therefore, the length of time for initial dosing must determined on a case-by-case basis.

After the initial dose of sulfur oxidizing bacteria have been added, maintenance doses may be required to maintain the population. Whether these are needed and the amount required will vary from facility to facility and sometimes from month to month. Factors that influence the size of maintenance doses will include the level of $BOD_5$ loading, and the size of the sulfur oxidizing population prior to maintenance dosing. Although the precise amount needed will have to be determined on a case-by-case basis, the inventor expects that about one to about three lbs of the preferred sulfur oxidizing bacteria culture per mgd ($1.27 \times 10^{11}$ to $3.81 \times 10^{11}$ cfu/mgd) to be sufficient in most wastewater treatment bodies.

In addition to treating sulfur odors, the present invention can also treat organic acid odors. Organic acids, such as acetic acid, butyric acid, isovaleric acid, and propionic acid, and their corresponding salts all have a rancid odor. However, these compounds can be oxidized by sulfur oxidizing bacteria such as *Paracoccus pantotrophus* using either oxygen $O_2$ or nitrate $NO_3^-$ as the terminal electron acceptor. For this biochemical oxidation to proceed, ORP levels should preferably be adjusted to between about −330 mV and about +100 mV. Subranges exist within this desired ORP range depending upon pH which may be adjusted as well. For pH values between about 6.0 to 7.0, the preferred ORP level is between about −175 mV to about +100 mV; for pH values between about 7.0 to about 7.5, the preferred ORP is between about −220 mV to about +75 mV, a particularly preferred range for paper industry applications; and for pH values between about 7.5 to about 8.2, the preferred ORP level is between about −330 mV to about −100 mV.

The biological oxidation of the organic acids will produce non-odor causing end products, carbon dioxide $CO_2$, water $H_2O$, and cell mass $C_5H_7O_2N$, if there is sufficient oxygen present in the wastewater. Where the reaction is completed with nitrate, the end products will also include nitrogen gas $N_2$. Unlike some other treatments for organic acid odors, undertreatment with bacteria such as *Paracoccus pantotrophus* will not lead to a worsening of the odors. If there are insufficient terminal electron acceptors in the wastewater, the bacteria will only oxidize part of the organic acids, which will simply result in a reduction of the concentration of odor causing species.

The inventor expects that average sulfur oxidizing populations of at least $1 \times 10^5$ cfu/ml will be desirable in most applications, and that populations of $1 \times 10^6$ to $1 \times 10^7$ cfu/ml or higher will be preferred. Concentrations of sulfur oxidizing bacteria of these levels will provide an additional benefit beyond the treatment of odors. They will also be effective in treating $BOD_5$, as illustrated in the examples discussed below.

Prior to treatment a candidate wastewater is tested for sulfur and organic acid compounds. The wastewater is adjusted to the desired pH, and several 250 mL samples are placed in different shake flasks. Varying quantities of an oxidizing agent such as nitrates or peroxides are added to the flasks in order to raise the ORP. A culture of sulfur reducing bacteria such as *Paracoccus pantotrophus* is added to each flask, and the ORP is measured immediately and again after the flask has shaken for four hours. ORP increases as the oxidizing agents are reduced by the bacteria so the later tests are usually higher. Successful tests should have a noticeable improvement in odors after four hours of shaking. Additionally, the flasks are analyzed for sulfides, sulfate and organic acid to ensure that the odor causing compounds have been removed.

Successful candidates should have less than 3.0 mg of butyric acid and less than 3.0 mg of butyric acid per liter of wastewater, less than 0.5 mg of sulfides per liter of wastewater, and less than 0.1 mg of mercaptans per liter of wastewater after four hours of shaking and at a pH of 7.0.

Particular examples and the results obtained in practicing a preferred embodiment of the invention are given below. There are, of course, alternate embodiments and applications, which should be obvious to those skilled in the art in view of the foregoing description and in view of the following examples, that are intended to be included within the scope of the claims which follow.

EXAMPLE I

The invention was tested a pulp and paper mill lagoon in Sasketchikan, Canada in the late spring and early summer. The mill operated a closed loop wastewater system where wastewater flows to a waster receiving pond (WRP). The WRP had a volume of 10 million gallons, and received a waste flow of 3 mgd. The nominal retention time was three days. The influent had an average chemical oxygen demand (COD) of 930 mg/L and an average effluent COD of 345 mg/L. Like $BOD_5$, COD measures the system's need for oxygen, but it takes into account the non-biological consumption of oxygen as well as biological consumers.

During the test, the WRP had an average of eight 25 horsepower aerators, which were rated to transfer a total of 8400 lbs. of oxygen per day. Using the influent and effluent COD values, the average oxygen demand was calculated to be about 14,000 lbs/day, so there was a continuous oxygen deficit. Under these conditions, the bacteria were undoubtedly using alternative electron acceptors in the metabolization of the $BOD_5$ sources in the wastewater, which as discussed above, can lead to the formation and buildup of odor causing compounds.

The mill had been experiencing daily hydrogen sulfide, bisulfide, and mercaptan odors in the vicinity of the WRP. The mill was unable to install additional aeration equipment, and it had unsuccessfully added various oxidants such as nitrates and hydrogen peroxide in the past without success.

Prior to the test, samples of the WRP wastewater were analyzed and found to have a pH of about 6.5, greater than 5 mg/L of hydrogen sulfide, greater than 12 mg/L of bisulfide, and greater than 2 mg/L of methyl mercaptans. During the test, sulfide levels ($H_2S$, $HS^-$, $S^{2-}$) were measured every five days using Standard Method 4500 $S^{2-}$ D, from the *Standard Methods for the Examination of Water and Wastewater*, 15th ed., APHA, which is hereby incorporated by reference in its entirety. Prior to the test, the sulfide concentration was found to range be 4.2 to 7.0 mg/L while these levels fell to between 0.1 and 1.2 mg/L during the test.

The pH of the WRP was raised to about 7.0 over three days by adding sodium hydroxide (NaOH). The ORP of the WRP was then raised from a normal reading of between −400 mV to −300 mV to levels above −300 mV by adding 24 mg of hydrogen peroxide per liter of WRP volume. As soon as the hydrogen peroxide was added, in excess of 300 lbs. of the preferred embodiment of the sulfur reducing bacterial culture as described in Table A above was added to the WRP. This amounted to an initial concentration of about 3.5 lbs. of culture per mgd and about 30 lbs. of culture per acre of the WRP surface area. The initial targeted count for the sulfur reducing bacteria, *P. pantotrophus* in this case, was about $4.4 \times 10^{11}$ cfu per mgd. This was a high dosage to compensate for the unknown growth rate of the bacteria in the environment.

After the initial dosage, additional culture was provided in maintenance dosages of 1 lb. of culture per mgd (about $1.27 \times 10^{11}$ cfu/mgd). Additionally, about 4 to 6 mg of 35% by weight hydrogen peroxide per liter of total WRP flow were added daily. Prior to this application, the mill had added hydrogen peroxide in quantities in excess of 24 mg/L without success.

By day 5 of the test, odors had noticeably diminished, and were completely absent to most subjective observers by day 10. Observations in all cases were made from a paved road about 100 feet from the WRP in the direction of the mill. Table B gives the objective data collected during this test.

TABLE B

| Day of Trial | pH, SU | Sulfide, mg/L | ORP, mV | $H_2O_2$ mg/L | Table A Bacterial Culture Added, lbs. (cfu) |
|---|---|---|---|---|---|
| −20 | 6.5 | 5.4 | −360 | 40 | 0 (0) |
| −15 | 6.7 | 7.0 | −380 | 25 | 0 (0) |
| −10 | 6.5 | 4.2 | −320 | 0 | 0 (0) |
| −5 | 6.7 | 6.0 | −410 | 0 | 0 (0) |
| 0 | 7.1 | 1.2 | −240 | 24 | >300 (>$3.81 \times 10^{13}$) |
| 5 | 7.4 | 1.4 | −130 | 4 | 3 ($3.81 \times 10^{11}$) |

TABLE B-continued

| Day of Trial | pH, SU | Sulfide, mg/L | ORP, mV | $H_2O_2$ mg/L | Table A Bacterial Culture Added, lbs. (cfu) |
|---|---|---|---|---|---|
| 10 | 7.3 | 0.1 | −150 | 5 | 3 ($3.81 \times 10^{11}$) |
| 15 | 7.4 | 0.3 | −170 | 7 | 1 ($1.27 \times 10^{11}$) |
| 20 | 7.4 | 0.5 | −90 | 6 | 1 ($1.27 \times 10^{11}$) |

EXAMPLE II

Figure 4:
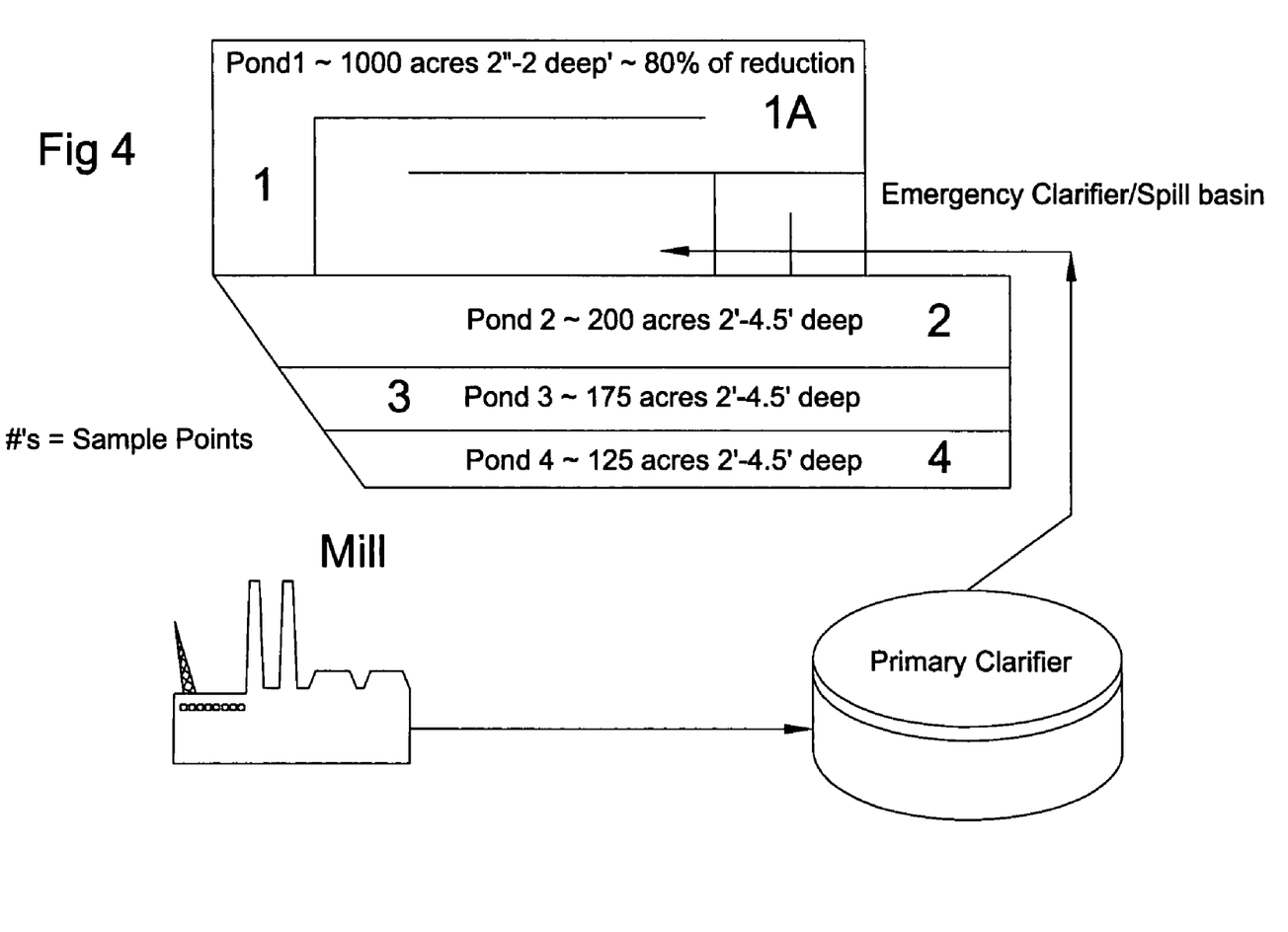
FIG. 4 is a schematic representation of the Florida wastewater facility where the invention was tested as described in Example II.
Figure 5:
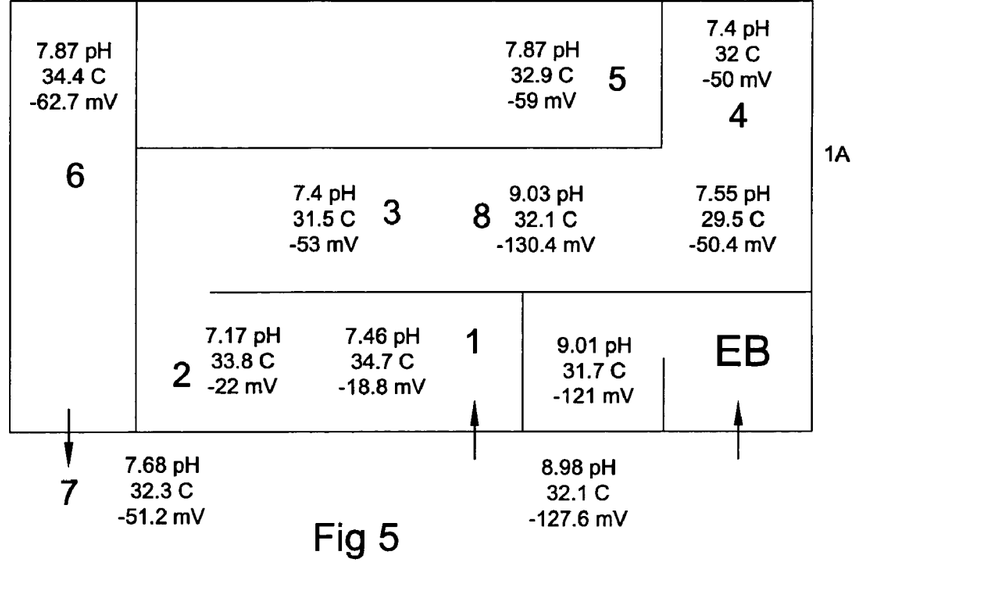
FIG. 5 is a graphical illustration of the different data collection points on lagoon A of example II at the beginning of month 2.
Figure 6:
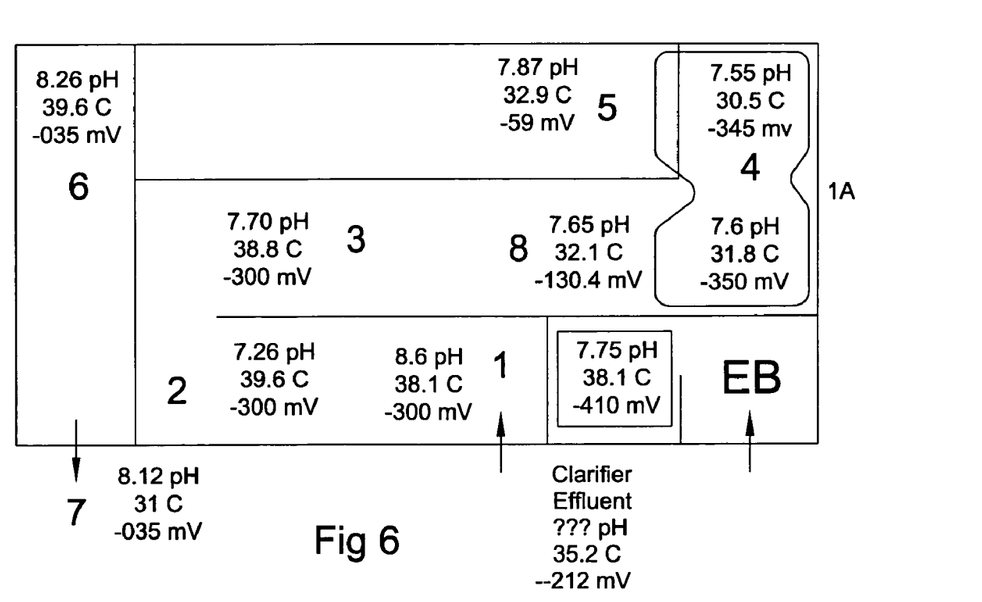
FIG. 6 is a graphical illustration of the different data collection points on lagoon A of example II at the end of month 2.
Figure 7:
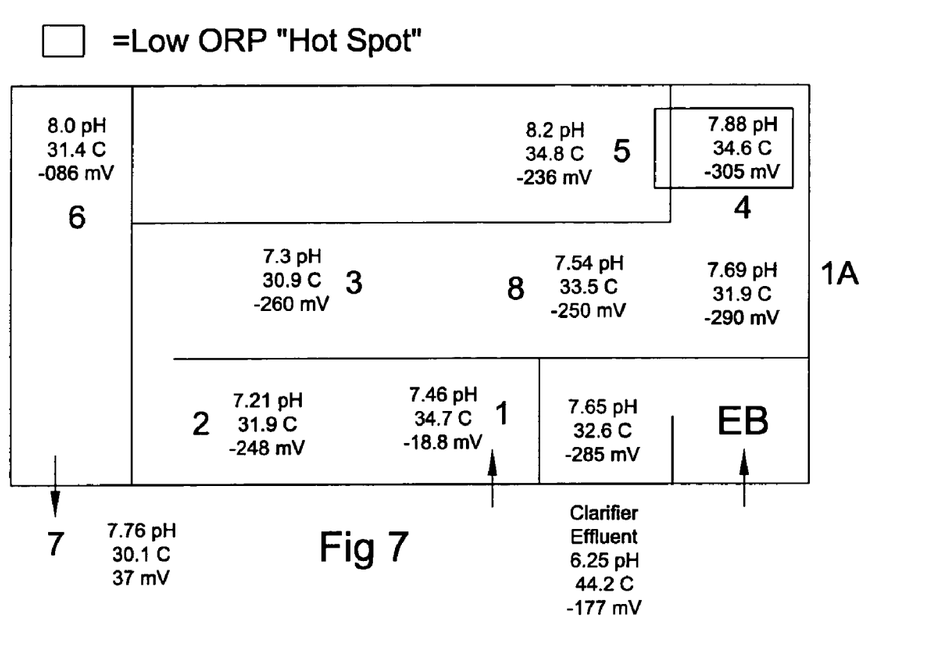
FIG. 7 is a graphical illustration of the different data collection points on lagoon A of example II at the beginning of month 3.
Figure 8:
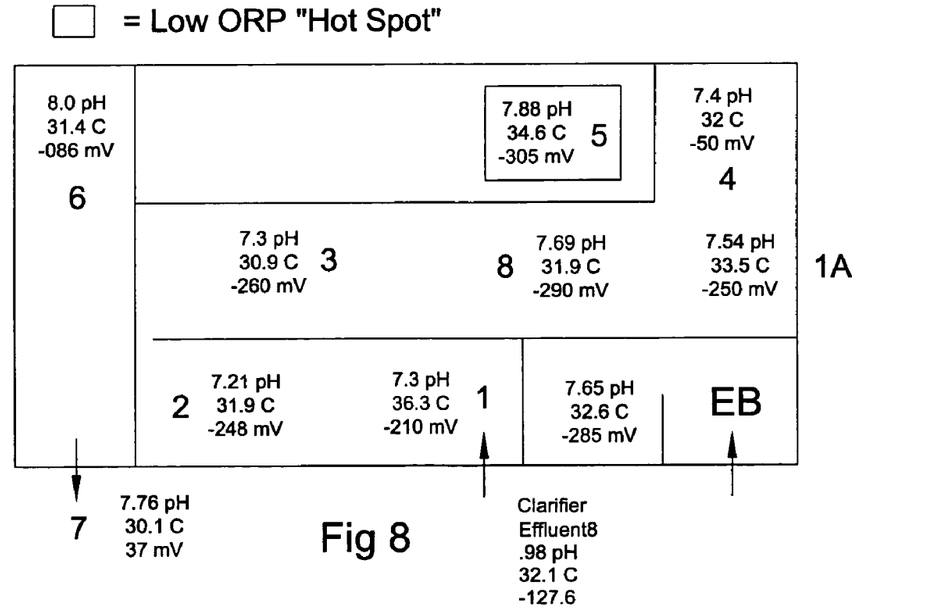
FIG. 8 is a graphical illustration of the different data collection points on lagoon A of example II at the end of month 3.
Figure 9:
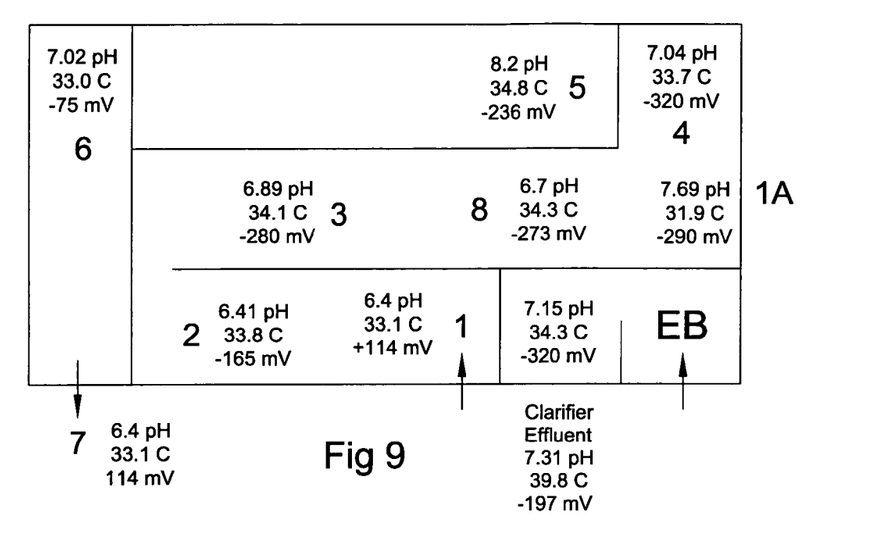
FIG. 9 is a graphical illustration of the different data collection points on lagoon A of example II at the beginning of month 4.

The invention also was tested at pulp and paper mill in Florida during the summer months. The wastewater treatment facility was set up as shown in FIG. 4. The facility consisted of four lagoons. Lagoon A covered 100 acres and contained 325 million gallons. Lagoon B covered 200 acres and contained 225 million gallons. Lagoon C covered 175 acres and contained 185 million gallons. Lagoon D covered 125 acres and contained 130 million gallons. Lagoon A is the only lagoon that was not aerated. Wastewater flowed from the mill to a primary clarifier to lagoon A to lagoon B to lagoon C to lagoon D and then it was discharged. The total retention time in the system was about 30 days. At the time of the test, lagoon A was operating at between about 30° to about 40° C. and historically received $BOD_5$ loadings of about 45,000 lbs/day.

Lagoon A was experiencing odor problems which had been unsuccessfully treated with sodium hypochlorite NaOCl and liquid sodium nitrate ($NaNO_3$). Subjective reporting indicated the presence of $H_2S$ and mercaptan odors. Objective data suggested that organic odors were likely present as well, but no these were not subjectively reported. Baseline data was gathered in the months prior to the test, and are reported below in Table C.

Treatment was commenced in Lagoon A by adding 330 lbs of $Ca(NO_3)_2$ of 70% by weight $Ca(NO_3)_2$ per day for seven days and a two day startup dosage of 1000 lbs of the bacterial culture described in Table A. The initial application was broadcast on the lagoon surface by airboat. Thereafter the inventor applied 25 lbs/day of the same culture for twenty-eight days. Approximately 28 days after the initial treatment, a survey of ORP, organic acids, and sulfur compounds was performed. The stations around lagoon A were marked for additional sampling. A comparison of the average data collected at Stations 1–8 to the average baseline data at the same points is provided below in Table D.

TABLE D

| | BASELINE DATA Averaged Data from 3 Surveys (24 Values) at Stations 1–8 over 3 Months Prior to Treatment | TEST RESULTS Averaged Data from of 4 Surveys (32 Values) at Stations 1–8 During Treatment | % Reduction |
|---|---|---|---|
| ph | 7.5 | 7.65 | <0.02> |
| ORP, mV | −304 | −230 | <24> |
| Sulfides, mg/L | 3.65 | 0.24 | 93 |
| Butyric Acid, mg/L | 6.65 | 0.18 | 97 |
| Propionic Acid, mg/L | 9.34 | 1.21 | 87 |
| DMDS mg/L | 3.36 | 0.14 | 96 |

Although the foregoing data indicated a substantial improvement from an analytical standpoint, especially in the removal of the major odor causing compounds, sulfide and mercaptans (dimethyl disulfide), minor but still detectable odors continued to emanate from lagoon A. It was believed that these were caused by "hot spots" of negative ORP located across lagoon A. To better monitor the conditions in lagoon A, data was examined from several different survey locations in the lagoon.

These tests revealed that conditions varied substantially within lagoon A. FIGS. 5–9 illustrate the points where data was gathered across lagoon A in months 2, 3, and 4 of the test, and the variances detected across lagoon A.

To treat the residual odors detected at the plant, the target ORP was raised to −200 mV at pH>7.0, and an ORP floor of −250 mV at pH 7.0 was established. If "hotspots" of depressed ORP were detected, spot applications of nitrate and bacterial cultures as disclosed in Table A were made to raise the local ORP. The spot dosages were determined on an individual case basis out by trial and error but were approximately 50 lbs. $NO_3^-$ per acre and about 10 lbs. of Table A bacterial culture per acre.

Subjective observations indicated that the lingering odor problems had been corrected. Objective data collected over the remainder of the test confirmed the subjective indications. Table E illustrates the reduction in organic acids, mercaptans, and sulfide levels during the remainder of the evaluation period. Additionally, Table E illustrates the significant ORP increase in the lagoon.

TABLE E

| | Baseline 3 Surveys - 24 Values | Evaluation Period 7 Surveys - 56 Values |
|---|---|---|
| pH, Avg. | 7.5 | 7.62 |
| Sulfide, mg/L Avg. | 3.65 | 0.78 |
| Total Organic Acids, mg/L Avg. | 36.70 | 17.40 |
| Total Mercaptans, mg/L Avg. | 4.39 | 0.49 |
| ORP, mV Avg. | −304 | −212 |

Prior to and throughout the test, data was collected on the growth of the sulfur oxidizing bacteria population in lagoon A. Prior to the test, population levels were consistently below $1 \times 10^3$ cfu/mL. The sulfur oxidizing bacteria population steadily increased during the test, as summarized in Table F below.

TABLE F

| | Concentration of Sulfur Oxidizing Bacteria, cfu/mL |
|---|---|
| Month 1 | $\sim 1 \times 10^4$ |
| Month 2 | $\sim 1 \times 10^5$ |
| Month 3 | $\sim 1 \times 10^5$ |
| Months 4–7 | $> 1 \times 10^6$ |

During the evaluation period, the mill wastewater system was monitored for removal of $BOD_5$ from lagoon A. Table G compares the average monthly influent and effluent $BOD_5$ levels in lagoon A over the six prior to the test to the average monthly influent and effluent levels during the test.

TABLE G

|  | Historical Influent BOD$_5$, lbs. | Test Influent BOD$_5$, lbs. | Historical Effluent BOD$_5$, lbs. | Test Effluent BOD$_5$, lbs. |
|---|---|---|---|---|
| Average | 41,011 | 40,323 | 9,150 | 7,545 |
| S. Deviation | 12,635 | 11,992 | 1,323 | 932 |

I claim:

1. A method for reducing odors in a wastewater treatment body comprising:
    establishing a pH in said body of at least about 6.0;
    establishing an oxidation reduction potential level in said body of at least about −330 mV; and
    establishing a sulfur oxidizing bacteria population in said body of at least about 1×10$^4$ colony forming units per milliliter, wherein said sulfur oxidizing bacteria includes a bacteria having ATCC number 35,512.

2. A method for reducing odors in a wastewater treatment body according to claim 1 wherein said sulfur oxidizing bacteria are selected from the genus *Paracoccus*.

3. A method for reducing odors in a wastewater treatment body according to claim 1 wherein said Oxidation Reduction Potential is established at a level of at least about −200 mV.

4. A method for reducing odors in a wastewater treatment body according to claim 3 wherein said sulfur oxidizing bacteria are selected from the genus *Paracoccus*.

5. A method for reducing odors in a wastewater treatment body according to claim 1 wherein said oxidation reduction potential is established by adding nitrates to said body.

6. A method for reducing odors in a wastewater treatment body according to claim 5 wherein said sulfur oxidizing bacteria are selected from the genus *Paracoccus*.

7. A method for reducing odors in a wastewater treatment body according to claim 5 wherein said oxidation reduction potential is established at a level of at least about −200 mV.

8. A method for reducing odors in a wastewater treatment body according to claim 7 wherein said sulfur oxidizing bacteria are selected from the genus *Paracoccus*.

9. A method for reducing odors in a wastewater treatment body according to claim 1, 2, 3, 4, 5, 6, 7, or 8, wherein said sulfur oxidizing bacteria population is at least about 1×10$^5$ colony forming units per milliliter.

10. A method for reducing odors in an open air wastewater treatment body comprising:
    establishing a pH in said open air body of at least about 6.0;
    establishing an oxidation reduction potential level in said open air body of at least about −330 mV; and
    establishing a sulfur oxidizing bacteria population in said open air body of at least about 1×10$^4$ colony forming units per milliliter, wherein said sulfur oxidizing bacteria includes a bacteria having ATCC number 35,512.

11. A method for reducing odors in an open air wastewater treatment body according to claim 9 wherein said sulfur oxidizing bacteria are selected from the genus *Paracoccus*.

12. A method for reducing odors in an open air wastewater treatment body according to claim 9 wherein said Oxidation Reduction Potential is established at a level of at least about −200 mV.

13. A method for reducing odors in an open air wastewater treatment body according to claim 12 wherein said sulfur oxidizing bacteria are selected from the genus *Paracoccus*.

14. A method for reducing odors in an open air wastewater treatment body according to claim 10 wherein said oxidation reduction potential is established by adding nitrates to said body.

15. A method for reducing odors in an open air wastewater treatment body according to claim 13 wherein said sulfur oxidizing bacteria are selected from the genus *Paracoccus*.

16. A method for reducing odors in an open air wastewater treatment body according to claim 14 wherein said oxidation reduction potential is established at a level of at least about −200 mV.

17. A method for reducing odors in an open air wastewater treatment body according to claim 15 wherein said sulfur oxidizing bacteria are selected from the genus *Paracoccus*.

* * * * *